United States Patent [19]

Taylor-McCord

[11] Patent Number: 5,604,200

[45] Date of Patent: Feb. 18, 1997

[54] WOUND THERAPEUTIC MIXTURE CONTAINING MEDICAL GRADE HYALURONIC ACID AND TISSUE CULTURE GRADE PLASMA-FIBRONECTIN IN A DELIVERY SYSTEM THAT CREATES A MOIST ENVIRONMENT WHICH SIMULATES IN UTERO HEALING

[76] Inventor: Darlene Taylor-McCord, 24666 Morningstar La., Dana Point, Calif. 92629

[21] Appl. No.: 236,176

[22] Filed: May 2, 1994

[51] Int. Cl.[6] .................... A61K 38/36; A61K 35/14; C08B 37/08; C07K 14/75

[52] U.S. Cl. .................... 514/8; 514/12; 514/21; 514/871; 530/382; 530/351; 536/55.1; 424/600

[58] Field of Search .................... 514/8, 12, 21, 514/871; 424/600; 530/381, 382, 829, 830, 851; 536/55.1

[56] References Cited

U.S. PATENT DOCUMENTS

| | | | |
|---|---|---|---|
| 3,887,703 | 6/1975 | Manoussos | 424/581 |
| 4,983,580 | 1/1991 | Gibson | 514/2 |
| 5,036,056 | 7/1991 | Kludas | 514/54 |

OTHER PUBLICATIONS

Br. J. Obstet. Gynaecol. "Biochemical Composition of Amniotic Fluid and Extraembryonic Coelomic Fluid In The First Trimester of Pregnancy" Campbell et al. 99: 563–565 1992.

Clark "Cutaneous Wound Repair" In Physiology, Biochemistry & Molecular Biology of The Skin ed. Goldsmith pp. 576–601 1991.

Doillon et al. "Collagen–based Wound Dressing: Effects of Hyaluronic Acid & Fibronectin on Wound Healing" Biomaterials 7 3–8 1986.

Repesh et al. "Fibronectin Involvement in Granulation Tissue & Wound Healing In Rabbits" J Histochem Cytochem 30(4) 351–358 1982.

Mast et al. "Scarless Wound Healing In The Mammalian Fetus" Surg. Gyn. Ob. 174(5) 441–451. 1992.

*Primary Examiner*—John L. LeGuyader
*Assistant Examiner*—Nancy J. Degen
*Attorney, Agent, or Firm*—Daniel L. Dawes

[57] ABSTRACT

A wound therapeutic mixture is formulated to work alone or in combination with human growth factors, and is useful for treatment of burns, open sores, incisions, and wounds. The mixture is comprised of a medical grade hyaluronic acid (hyaluronan) and tissue culture grade plasma-fibronectin in combination with calcium, phosphate, uric acid, urea, sodium, potassium, chloride, and magnesium, all elements found in amniotic fluid. The mixture creates a moist healing environment which simulates the fetal in utero wound healing matrix. The therapeutic mixture can be sterile or contain an FDA acceptable preservative system. The compositions may be in the form of a liquid, creme, ointment, gel, hydrogel, hydrocolloid or dressing.

15 Claims, 1 Drawing Sheet

WOUND THERAPEUTIC MIXTURE CONTAINING MEDICAL GRADE HYALURONIC ACID AND TISSUE CULTURE GRADE PLASMA-FIBRONECTIN IN A DELIVERY SYSTEM THAT CREATES A MOIST ENVIRONMENT WHICH SIMULATES IN UTERO HEALING

BACKGROUND OF INVENTION

1. Field of the Invention

This invention relates the treatment of burns, open sores, incisions and wounds. In particular it relates to topical wound therapeutic formulations containing a hyaluronic acid (hyaluronan) and plasma-fibronectin in combination with elements found in amniotic fluid which simulates the fetal in utero wound healing matrix.

2. Description of the Prior Art

The "greying of America" is well documented. People are living longer and have expectations for a quality life as well as well as a long life.

People afflicted with long term illness run the risk of getting bed sores, pressure sores and a myriad of skin irritations and chronic wounds.

Looking at the treatment figures for pressure ulcers, just a small part of the entire market, one can quickly see that there is a need to develop products that will effectively treat patients with long term illnesses.

As part of a study using AMA data on admissions to acute hospitals to derive the number of patients at risk of pressure ulcers, the statistics and forecasts are as follows:

| PATIENTS 1000's | 1989 | 1990 | 1995 | 2000 | 2005 |
| --- | --- | --- | --- | --- | --- |
| STAGE 1 | 539 | 547 | 596 | 656 | 718 |
| STAGE 2 | 779 | 790 | 861 | 947 | 1037 |
| STAGE 3 | 180 | 182 | 199 | 219 | 239 |
| STAGE 4 | 180 | 182 | 199 | 219 | 239 |
| TOTAL | 1677 | 1701 | 1853 | 2040 | 2233 |

Cancer and the use of radiation to treat the disease is on the rise. In 1960, the lifetime risk of developing breast cancer was 1 in 20. In 1991, the risk is 1 in 8. In 1992 180,000 American women will be diagnosed with breast cancer (one every 3 minutes). This drastic increase in breast cancer is enjoined by a myriad of other cancers which are being treated with radiation and the result is a need for an effective topical treatment to reduce the risk and effect of burn.

Wound healing after surgical intervention has been problematic in all recorded history. The benefits of surgery, even in life-threatening situations, are offset by the formation of disfiguring scar tissue.

Adult wound repair is characterized by fibrosis, scarring, and sometimes by contracture. The results of this deforming process affect every form of surgery and can have devastating consequences. In contrast fetal wound healing proceeds without such fibrosis or scar formation, Michael T. Longaker, M.D., Ernie S. Chiu, B.S., N. Scott Adzick, M.D., Michael Stern, D.D.S., Michael R. Harrison, M.D., and Robert Stern, M.D., *Studies in Fetal Wound Healing, V. A Prolonged Presence of Hyaluronic Acid Characterizes Fetal Wound Fluid,* Ann Surg, April 1991, pp 292–296.

There is great value in the scientific exploration of the fetal environment. As researchers isolate proteins, carbohydrates and other elements, we gain insight into the delicate balance that creates the only perfect new-life support system capable of facilitating rapid new cell growth and differentiation.

With amniotic fluid, the whole is truly greater than the sum of its parts. It is known that hyaluronic acid bonds with fibronectin and together they have a powerful effect on the body's cellular matrix. It is also known that urea, produced by the fetus has an effect on cell migration. Elements such as glucose, protein, sodium, potassium, calcium, magnesium, phosphate and chloride that form the amniotic fluid, work together with an inseparable bond and synergy.

The prior art has isolated key elements of the amniotic fluid and disclosed products for the treatment of wounds, but none have sought the synergy of elements that create the only perfect healing environment.

Several prior art patents disclose therapeutic formulations including hyaluronic acid. Lindblad, "Hyaluronic Acid Preparation used for Treating Inflammations of Skeletal Joints"; U.S. Pat. No. 4,801,619 disclosed the use of hyaluronic acid for intra-articular administration for the treatment of steroid arthropathy and progressive cartilage degeneration caused by proteoglycan degradation. Langerman, "Spare Parts for Use in Ophthalmic Surgical Procedures" U.S. Pat. No. 4,888,016 disclosed the use of hyaluronic acid in ophthalmic surgery as an artificial "spare part" for surgical implantation in the eye during an extracapsular cataract extraction. Alvarez, "Three Step Wound Treatment Method and Dressing Therefor"; U.S. Pat. No. 4,813,924 disclosed the use of hyaluronic acid in the third step of a three step treatment. The invention calls for the hyaluronic acid to be in a hydrocolloid dressing which will provide controlled delivery over a period of 24 to 96 hours to promote thickening of the epidermal cells, thus strengthening the wound. Balazs et al, "Cross-Linked Gels of Hyaluronic Acid and Products Containing Such Gels"; U.S. Pat. Nos. 4,582,865, 4,636,524, and 4,636,865 disclosed the use of cross-linked gels of hyaluronic acid as a drug delivery system.

None of these prior art references claim to use medical grade hyaluronic acid and tissue culture grade plasma-fibronectin in the treatment of burns, open sores, incisions, and wounds and there is no combination with calcium, phosphate, uric acid, urea, sodium, potassium, chloride, and magnesium, which combine to simulate amniotic fluid.

Several prior art patents disclose therapeutic formulations including fibronectin. Gibson et al, "Wound Healing Composition and Method"; U.S. Pat. No. 5,053,388 disclosed the use of a solution containing a protein crosslinking compound such as dimethyl pimelimidate dihydrochloride, followed by fibronectin to improve wound healing particularly wounds of the eye. Reich, "Wound Healing Dressing and Method"; U.S. Pat. 4,973,466 discloses the use of a wound healing dressing comprised of flocculating fibronectin that produce a water-swellable gel useful in promoting healing of corneal, scleral dermal, incisional wounds and lesions obtained in keratorefractive surgeries. Silver et al., "Biodegradable Matrix and Methods for Producing Same," U.S. Pat. No. 4,970,298 discloses a biodegradable matrix which comprises collagen, hyaluronic acid and fibronectin which enhance healing of wounds. Collagen, which is oversecreted by the body in response to an injury or wound, is know to be responsible for scar formation. Georgalas et al., "Skin Treatment Composition and Method for Treating Burned Skin," U.S. Pat. 4,839,019, discloses a composition which counteracts moisture loss and promotes healing of burned or sunburned skin comprised of polyglycerylmethacrylate, glycerine, allantoin, panthenol, amino acid complex, and fibronectin.

None of these references claim to use medical grade hyaluronic acid and tissue culture grade plasma-fibronectin in the treatment of burns, open sores, incisions, and wounds and there is no combination with calcium, phosphate, uric acid, urea, sodium, potassium, chloride, and magnesium, which combine to simulate amniotic fluid.

What is needed is a delivery system for medical grade hyaluronic acid and tissue culture grade plasma-fibronectin that is compatible with needs of the wound environment, and creates a moist healing environment that replicates the amniotic fluid that supports rapid, scar-free healing in utero.

BRIEF SUMMARY OF THE INVENTION

The invention relates to formulations containing a medical grade hyaluronic acid and tissue culture grade plasma-fibronectin as found in amniotic fluid in high levels and responsible for rapid, scar-free healing. The mixture is combined with calcium, phosphate, uric acid, urea, sodium, potassium, chloride and magnesium which simulate amniotic fluid to create a unique therapy for the management of burns, open sores, incision and wounds. The rapid healing action of medical grade hyaluronic acid and tissue culture grade plasma-fibronectin combined with a delivery system formed by calcium, phosphate, uric acid, urea, sodium, potassium, chloride and magnesium, all elements found in amniotic fluid, has a unique synergy that is effective in the treatment of burns, open sores, incisions and wounds.

The invention is used for wound therapeutic formulations useful for topical application, useful for treating burns, traumatic damage caused by irradiation of the skin, the deleterious effects of open sores, incisions and wounds on skin in a mixture which simulates the fetal in utero wound healing matrix in a safe and effective amount of a topical carrier.

More specifically the invention is a mixture for the treatment of burns, open sores, incisions and wounds in an environment for optimum healing comprising medical grade hyaluronic acid, tissue culture grade plasma fibronectin and a topical solution. The medical grade hyaluronic acid and tissue culture grade plasma fibronectin are carried by the topical solution to the site of the burns, open sores, incisions and wounds to create the environment for optimum healing.

The further comprises elements for simulating amniotic fluid to treat burns, open sores, incision and wounds. The elements comprise a mixture of constituents selected from the group of calcium, phosphate, uric acid, urea, sodium, potassium, chloride and magnesium.

In one embodiment the topical solution comprises a pharmaceutically acceptable carrier. In another embodiment the topical solution comprises a cosmetically acceptable carrier.

In specific terms the medical grade hyaluronic acid comprises by weight 0.01% to 2.00% of the mixture. The tissue culture grade plasma-fibronectin comprises by weight 0.05% to 2.00% of the mixture. The topical solution comprises by weight of the mixture: 0.01% to 1.50% calcium; 0.01% to 0.10% phosphate; 0.01% to 2.00% uric acid; 0.01% to 2.00% urea; 0.02% to 1.50% sodium; 0.01% to 0.10% potassium; 0.01% to 0.70% chloride; and 0.001% to 0.01% magnesium.

In the best mode the medical grade hyaluronic acid comprises by weight 0.10% to 1.50% of the mixture. The tissue culture grade plasma-fibronectin comprises by weight 0.020% to 1.50% of the mixture. The topical solution comprises by weight of the mixture 0.50% to 1.00% calcium; 0.02% to 0.07% phosphate; 0.05% to 0.50% uric acid; 0.05% to 50% urea; 0.07% to 1.00% sodium; 0.02% to 0.06% potassium; 0.02% to 0.08% chloride; and 0.001% to 0.006% magnesium.

The mixture further comprises pharmaceutical/cosmetic compositions, and skin cleaning compositions.

The invention is also characterized as an improvement in a method of healing comprising the delivery of medical grade hyaluronic acid and a tissue culture grade plasma fibronectin in a topical solution to a burn, open sore, incision or wound so that a moist environment is created. As a result, optimum healing without minimal scarring is realized. The delivering of this mixture simulates the environment of amniotic fluid within the moist environment.

The invention can better be understood by viewing the following drawings in connection with the following detailed description and examples.

DETAILED DESCRIPTION OF THE PREFERRED EMBODIMENTS

Figure 1:
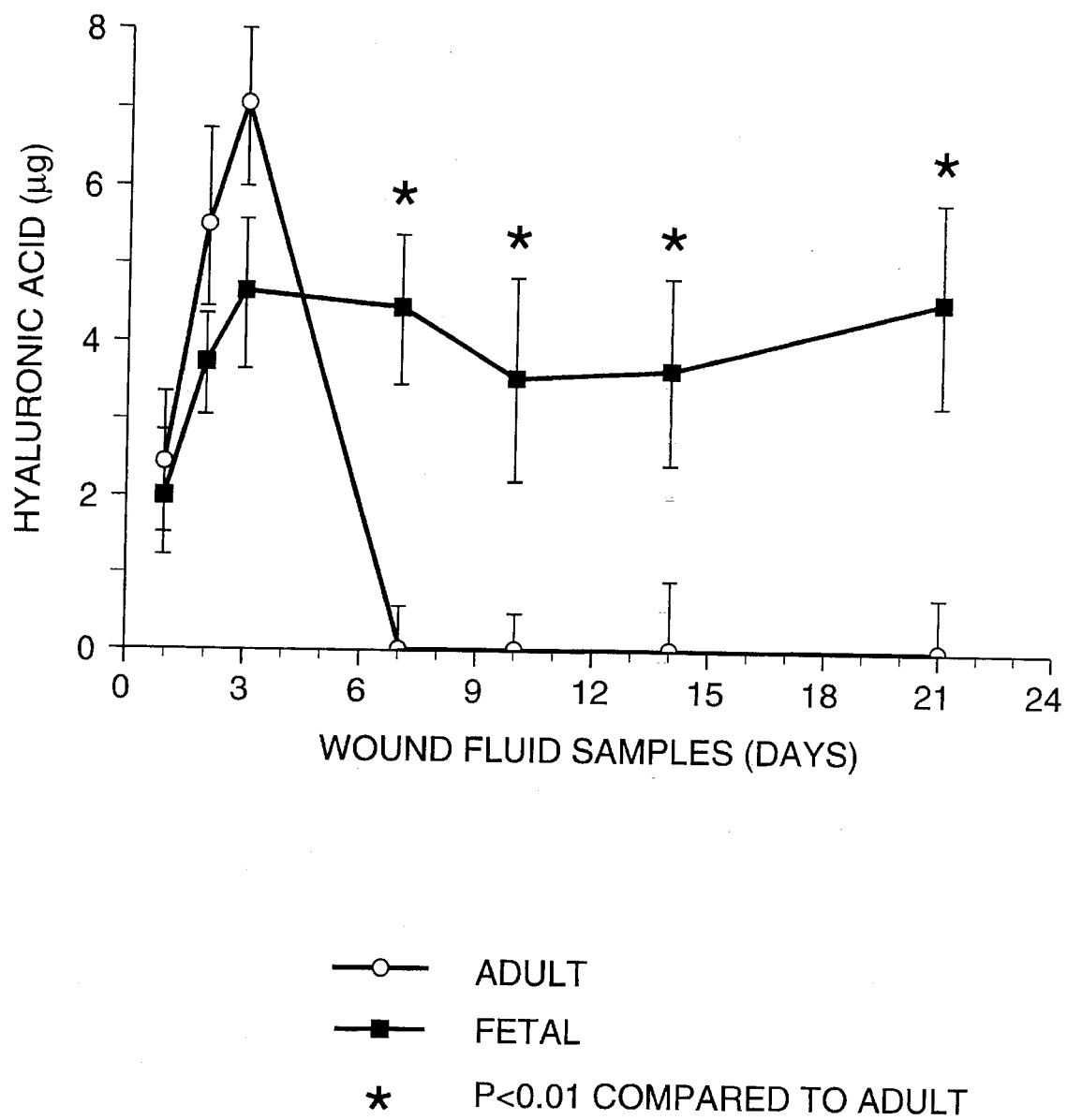
FIG. 1 is a graph depicting relative amounts of fibronectin and hyaluronic acid observed in fetal wound healing as a function of time.

The invention is a means for delivery of medical grade hyaluronic acid and a tissue culture grade plasma fibronectin in a topical solution that simulates amniotic fluid provides for the treatment of burns, open sores, incisions and wounds in an environment that is moist and creates a "womb" for optimum healing.

Researchers, surgeons, and the medical community at large have long sought to find the key to a scar-free healing process. There are many manufacturers providing hyaluronic acid. The grade of hyaluronic acid is important to efficacy of products produced under the invention and the lessor grades are of little or no value except for cosmetic claims. The invention characterizes medical grade hyaluronic acid as a hyaluronic acid that, after undergoing biological testing, has the following or better test results:

| TEST | RESULT |
| --- | --- |
| Microbial Bioburden | None observed |
| Endotoxin | <0.07 EU/mg NaHy |

Fibronectic for the purposes of the invention has a purity of at least 90% as indicated by SDS page.

In accordance with the invention, there is provided herein formulations useful for topical application comprising medical grade hyaluronic acid and tissue culture grade plasma-fibronectin in combination with calcium, phosphate, uric acid, urea, sodium, potassium, chloride, and magnesium, all elements healing matrix and a safe and effective amount of a topical carrier, in combinations described below.

Analysis of Amniotic Fluid

Amniotic fluid is the life support system that cradles the fetus in its mother's womb. The composition of amniotic fluid varies slightly from pregnancy to pregnancy, but there are basic elements set forth in Table I, which represents the work of Harry F. Weisberg, M.D., *Clinical Chemical Analyses of Sixty-two Amniotic Fluids from Women in Early Pregnancy, Amniotic Fluid,* Wiley Biomedical-Health Publications, 1971, pp 49.

The statistical analysis represented in Table I is based on sixty-two women, ages 14 to 44 years, admitted at 9 to 24 weeks gestation for therapeutic abortion by hypertonic saline. The vast majority of the amniotic fluid was obtained by transvaginal (transcervical) amniocentesis. The type of procedure was the choice of the attending obstetrician. Adequate quantities (50–100 ml) of amniotic fluid were aspirated by syringe and sent to the laboratory for centrifugation.

TABLE I

Summary of Data on Various Parameters (Determined and Calculated) for Amniotic Fluid.
Done on Technicon AutoAnalyzer Equipment.

| PARAMETER | X +/− SD (range) |
|---|---|
| I. Direct determination: | |
| Total protein* (g/dl) | 0.76 +/− 0.23 (0.2–1.7) |
| Albumin* (g/dl) | 0.48 +/− 0.14 (0.1–0.8) |
| Calcium* (mg/dl) | 7.08 +/− 0.55 (5.9–8.6) |
| Phosphate (mg/dl) | 3.04 +/− 0.77 (1.4–5.7) |
| Cholesterol* (mg/dl) | 19.6 +/− 10.2 (2–60) |
| Uric Acid* (mg/dl) | 4.08 +/− 1.2 (1.8–9.0) |
| Creatinine* (mg/dl) | 0.75 +/− 0.16 (0.5–1.7) |
| Total Billirubin* (mg/dl) | 0.23 +/− 0.14 (0–1.0) |
| Alk. Phosphatase* (U/liter) | 26.8 +/− 14.7 (5 70) |
| CK* (U/liter) | 39.6 +/− 11.9 (20–65) |
| LD* (U/liter) | 98.5 +/− 42.4 (20–175) |
| AST* (U/liter) | 23 +/− 11.4 (2–72) |
| Glucose* (mg/dl) | 44.3 +/− 11.4 (20–65) |
| Urea N* (mg/dl) | 9.1 +/− 2.1 (5–14) |
| Sodium* (mmol/liter) | 136.2 +/− 3.8 (130–150) |
| Potassium* (mmol/liter) | 3.7 +/− 0.18 (3.3–4.3) |
| Chloride* (mmol/liter) | 112.4 +/− 4.1 (106–126) |
| "CO(2)" (mmol/liter) | 16-1 +/− 2.8 (−25) |
| Calcium (At Ab) (mg/dl) | 0.67 +/− 0.78 (6.1–8.5) |
| Magnesium (At Ab) (mmol/liter) | 0.67 +/− 0.08 (0.47–0.8) |
| Osmolality (mosmol/kg) | 276.3 +/− 11.3 (257–306) |
| II Calculated Values: | |
| "Cation balance" (mmol/liter) | −6.6 +/− 3.1 (115.1–0.7) |
| Na/K cation (32.4–41.7) | 36.7 +/− 1.9 |
| Water Content (g/dl) (98.5–99.1) | 98.75 +/− 0.18 |
| Total bilirubin/total protein | 0.296 +/− 0.130 (0.111–0.875) |
| Total bilirubin/albumin | 0.489 +/− 0.260 (0–1.667) |

TABLE I-continued

Summary of Data on Various Parameters (Determined and Calculated) for Amniotic Fluid.
Done on Technicon AutoAnalyzer Equipment.

| PARAMETER | X +/− SD (range) |
|---|---|
| 450 nm | 0.111 +/− 0.038 (0.039–206) |
| 450/total bilirubin | 0.564 +/− 0.19 (0.308–1.22) |
| 450/total protein | 0.153 +/− 0.046 (0.070–0.293) |
| 450/albumin | 0.245 +/− 0.078 (0.134–0.524) |

Table I provides a broad view of the substances found within amniotic fluid. Further breakdown finds the presence, in elevated levels as compared to adults, of hyaluronic acid and fibronectin. These two substances have been shown to be responsible for the rapid cell growth and healing that is unique to the in utero experience.

Hyaluronic Acid

The key to solving the problems related to wound healing and the elimination of scarring lies within the uterus of a pregnant woman. Until recently this inaccessible area was guarded by the fetus. Very little was understood about the composition of the amniotic fluid or its vital role in the development process.

This situation has changed drastically in the past few years. Over the past few years, safe amniocentesis has become a reality, a development that was made possible by the development of accurate ultrasound monitoring procedures. Amniotic fluid samples can now be obtained for direct analysis, and have yielded a rich harvest of diagnostically helpful information, Merton Sandlet, *Amniotic Fluid and Its Clincal Significance,* Marcel Dekker, Inc. NY and Basel, Preface, 1981.

One of the most important scientific discoveries coming from the study of the fetus and its amniotic environment is that wounds created in utero heal rapidly and without scarring, fibrosis or inflammation. It is a process fundamentally different from adult wound heal, Michael T. Longaker, N. Scott Adzick, Jackson L. Hall, Susan E. Stair, Timothy M. Crombelholme, Brian W. Duncan, Scott M. Bradley, Michael R. Harrison, and Robert Stern, *Studies in Fetal Wound Healing, VII, Fetal Wound Healing May be Modulated by Hyaluronic Acid Stimulation Activity in Amniotic Fluid,* Journal of Pediatric Surgery, Vol. 25, No. 4 (April), 1990, pp 430–433.

Tissue repair in the mammalian fetus is fundamentally different than normal adult healing. In adult humans, injured tissue is repaired by collagen deposition, collagen remodeling and eventual scar formation, whereas fetal wound healing appears to be more of a regenerative process with minimal or no scar formation. The adult wound heals by the replacement of normal dermis with a scar that consists of excessive and abnormally organized collagen. In marked contrast, the fetal wound contains a persistent abundance of hyaluronic acid while collagen deposition is rapid and nonexcessive, Bruce A. Mast, M.D., Robert F. Diegelmann, Ph.D., Thomas M. Krummel, M.D., and I. Kelman Cohen, M.D., *Scarless Wound Healing in the Mammalian Fetus,* Surg. Gyn. and Ob., Vol. 174, PP 441–451, May 92.

What is known is that hyaluronic acid has a definite role in harnessing and manipulating the natural reparative capacity of tissue fibroblasts and the hyaluronic acid protein complexes play a significant role in vivo organization or scar tissue, D.A.R. Burd, R. M. Greco, S. Regaurer, M. T. Longaker, J. W. Siebert and H. G. Garg, *Hyaluronan and Wound Healing: a New Perspective*, Journal of Plastic Sutery, 1991, pp 579–584.

Hyaluronic acid has played a very limited role in the care and treatment of burns, open sores, incisions and wounds because there has not been an effective delivery system that could deliver medical grade hyaluronic acid, which is found in abundance in amniotic fluid, to the wound site in a manner that replicated the moist environment and the other healing benefits discovered in amniotic fluid.

Other researchers and members of the medical community have analyzed amniotic fluid for the answers to rapid, scar-free wound healing characteristic of the in utero environment. This phenomena was first observed clinically at the University of California, San Francisco in their fetal treatment program, Harrison MR, Adzick NS., *The Fetus As a Patient: Surgical Considerations*, Ann Surg 1991, pp 13: 279–290.

The fetal wound healing process may represent a paradigm for ideal tissue repair, N. Scott Adzick, M.D. and Michael T. Longaker, M.D., *Scarless Fetal Healing: Therapeutic Implications*, Ann. Surgery, Jan. 1992, pp 3–7. A wound is a discontinuity in tissue integrity and healing is the process of reconstituting that integrity. Scarring is the result of the failure of this process to achieve the complex degree of organization that occurs in uninjured tissue, D. Andrew R. Burd, John W. Siebert, H. Paul Ehrlich and Hari G. Garg, *Human Skin and Post-Burn Scar Hyaluronan: Demonstration of the Association with Collagen and other Proteins*, Matrix, Vol. 9/1989, pp 322–327.

The wound healing process is significantly different in adults as compared to the healing that takes place in amniotic fluid. Adult wound healing is characterized by sharply increased levels of hyaluronic acid during the first three days. By the seventh day, hyaluronic acid is not detectable. In adults, wound healing is believed to be accomplished by high levels of collagen instead of hyaluronic acid, and it is further believed that it is the collagen that is responsible for scarring.

Fetal wound healing is characterized by sharply increased levels of hyaluronic acid during the first three days, but, unlike adult wound healing the level of hyaluronic acid remains elevated for 21 days. These findings are the result of research conducted by Michael T. Longaker, M.D. Ernie R. Harrison, M.D., and Robert Stern, M.D. and reported in an article titled *Studies in Fetal Wound Healing: V. A. Prolonged Presence of Hyaluronic Acid Characterizes Fetal Wound Fluid*, in Ann. Surg., April 1991, pp 292–296. The graph of their findings as published is shown in FIG. 1.

Fibronectin

Fibronectin plays a major role in all wound healing and promotes epithelial and endothelial cell migration within the wound site. It is involved in the adhesion and extension of epithelial cells and in the process of reepithelialization.

Hyaluronic acid and fibronectin are macro-molecular regulators that bind during inflammation and wound healing. During the complicated multi-step process of wound healing the extracellular matrix is sequentially remodelled and rebuilt by the concentrated action of different cell types and their products. The wound becomes a transitory organ whose function is to successively remodel a series of increasingly complex extracellular matrices. The matrix develops sequentially from a lesion (a void), to a platelet plug, to a fibrin (blood) clot, to a relatively loose matrix of glycosaminoglycans and collagen, to a denser granulation tissue, and then to the final repaired tissue.

Fibronectin and hyaluronic acid are found in large amounts in dermis during embryonic development and play an important role in skin development, Charles J. Dillion and Frederick H. Silver, *Collagen-based wound dressing: Effects of hyaluronic acid and fibronectin on wound healing*, Biomaterials, 1986, Vol 7, pp 3–8.

The healing process of the fetus is controlled by high levels of hyaluronic acid and fibronectin. In the adult healing process there is an overproduction of collagen which leads to the formation of scar tissue. The topical addition of hyaluronic acid and fibronectin in the wound bed will alter the adult healing process and facilitate accelerated healing and reduce the formation of scar tissue.

Test results all support the conclusion that human fibrinogen specifically binds hyaluronic acid and show the feasibility of the role of these two macromolecules in wound healing. The hyaluronic-fibrinogen interaction may be important or even necessary for successful wound healing, Paul H. Weigel, Stephen J. Front, Robert D. LeBoeuf, and Cad T. McGary, *The Specific Interaction between Fibrin(ogen) and Hyaluronan: Possible Consequences of Hemostasis, Inflammation and Wound Healing*, The Biology of Hyaluronan, Wiley-Interscience Publications, Ciba Foundation Symposium 143, 1989, pp 248–285.

Table II is the result of research performed by Frederick Ginnell, *Fibronectin and Wound Healing*, reported in the Journal of Cellular Biochemistry 26, pp 107–119.

TABLE II

FUNCTIONS OF FIBRONECTIN IN CUTANEOUS WOUND HEALING

| Cell Type | Function | | |
|---|---|---|---|
| Platelets | Spreading | | |
| Neutrophils | Adhesion, | migration, | chemotaxis |
| Monocytes | Adhesion, phagocytosis, factors | migration, secretion | chemotaxis, of growth |
| Fibroblasts | Adhesion, phagocytosis, | migration, matrix | chemotaxis, organization |
| Endothelial cells | Adhesion, | migration, | chemotaxis |
| Epidermal cells | Adhesion, basement | migration, membrane | phagocytosis, organization |
| Bacteria | Tissue colonization | | |

The invention combines the basic amniotic fluid components with the key component responsible for wound healing in utero (hyaluronic acid and fibronectin) in a formulation that simulates the moist "womb" environment and provides for the delivery of medical grade hyaluronic acid to the burn, open sore, incision or wound for the period of time necessary to modulate adult wound healing and reduce healing time and scarring.

Topical Compositions

In addition to the active agents of medical grade hyaluronic acid, tissue culture grade plasma-fibronectin, calcium, phosphate, uric acid, urea, sodium, potassium, chloride, and magnesium, all elements found in amniotic fluid, the compositions of the invention contains a safe and effective amount of an acceptable topical carrier. The term "acceptable topical carrier" encompasses both pharmaceutically-acceptable carriers and cosmetically-acceptable carriers, and encompasses substantially non-irritating compatible components (either taken alone or in mixtures) which are suitable for delivering the active components to the skin. The term "compatible," as used herein, means that the components of the carrier must be capable of being commingled with medical grade hyaluronic acid and tissue culture grade plasma-fibronectin, combined with calcium, phosphate, uric acid, urea, sodium, potassium, chloride, and magnesium, all elements found in amniotic fluid, in a manner such that there is no interaction which would substantially reduce the efficacy of the composition during use for protecting the skin from the effects of burns, open sores, incision and wounds. These carriers must, of course, be of sufficiently high purity and sufficiently low toxicity to render them suitable for chronic topical administration to the skin of humans or lower animals. The term "safe and effective amount" of carrier means an amount sufficient to deliver the medical grade hyaluronic acid and tissue culture grade plasma-fibronectin to the skin, but not so much as to cause any side effects or skin reactions.

The topical compositions of the invention contain in combination generally from about (all percentages and ratios herein are by weight, unless otherwise specified):

1) 0.01% to 2.00% (preferably from about 0.10% to 1.50%) medical grade hyaluronic acid;
2) 0.05% to 2.00% (preferably from 0.020% to 1.50%) tissue culture grade plasma-fibronectin;
3) 0.01% to 1.50% (preferably from 0.50% to 1.00%) calcium;
4) 0.01% to 0.10% (preferably from 0.02% to 0.07%) phosphate;
5) 0.01% to 2.00% (preferably from 0.05% to 0.50%) uric acid;
6) 0.01% to 2.00% (preferably from about 0.05% to 1.50%) urea;
7) 0.02% to 1.50% (preferably from about 0.07% to 1.00%) sodium;
8) 0.01% to 0.10% (preferably from about 0.02% to 0.06%) potassium;
9) 0.01% to 0.70% (preferably from about 0.02% to 0.08%) chloride; and/or
10) 0.001% to 0.01% (preferably from about 0.001% to 0.006%) magnesium.

Variations in formulation of these carriers will result in a wide variety of products which fall within the scope of the invention. Thus it is to be understood that these constituents may be added in various combinations both as to amounts as well as to the type of constituents in any manner consistent with the spirit of the teachings of the invention.

These product types can be divided into two classes: pharmaceutical/cosmetic compositions and cleaning compositions.

Pharmaceutical/Cosmetic Compositions

The pharmaceutical/cosmetic compositions of the invention may be made into a wide variety of product types. These include, for example, lotions, creams, gels, sprays, ointments, rinses, hydrocoloids and dressings.

Cleaning Compositions

The skin/hair cleaning compositions of the invention comprise, in addition to medical grade hyaluronic acid, tissue culture grade plasma-fibronectin, sodium chloride, polymer, and allantoin, a cosmetically-acceptable surfactant. The term "cosmetically-acceptable surfactant" refers to a surfactant which is not only an effective skin/hair cleanser, but also can be used without undue toxicity, irritation, allergic response, and the like. Furthermore, the surfactant must be capable of being commingled with medical grade hyaluronic acid, tissue culture grade plasma-fibronectin, calcium, phosphate, uric acid, urea, sodium, potassium, chloride, and magnesium in a manner such that there is no interaction which would substantially reduce the efficacy of the composition for protecting the skin/hair.

The skin/hair cleansing compositions of the invention contain generally from about (all percentages and ratios herein are by weight, unless otherwise specified):

1) 0.01% to 2.00% (preferably from about 0.10% to 1.50%) medical grade hyaluronic acid;
2) 0.05% to 2.00% (preferably from 0.20% to 1.50%) tissue culture grade plasma-fibronectin;
3) 0.01% to 1.50% (preferably from 0.50% to 1.00%) calcium;
4) 0.01% to 0.10% (preferably from 0.02% to 0.07%) phosphate;
5) 0.01% to 2.00% (preferably from 0.05% to 0.50%) uric acid;
6) 0.01% to 2.00% (preferably from about 0.05% to 1.50%) urea;
7) 0.02% to 1.50% (preferably from about 0.07% to 1.00%) sodium;
8) 0.01% to 0.10% (preferably from about 0.02% to 0.06%) potassium;
9) 0.01% to 0.70% (preferably from about 0.02% to 0.08%) chloride; and/or
10) 0.001% to 0.01% (preferably from about 0.001% to 0.006%) magnesium.

The cleaning compositions of the invention may be made into a wide variety of product types. Variations in formulation of these cleaning compositions will result in a wide variety of products which fall within the scope of the invention. Thus it is to be understood that these constituents may be added in various combinations both as to amounts as well as to the type of constituents in any manner consistent with the spirit of the teachings of the invention. These products include, for example, body lathers, facial lathers, shampoos, and toilet bars.

EXAMPLE I—A therapeutic skin lotion

A therapeutic skin lotion is prepared by combining the following components utilizing conventional mixing techniques.

| INGREDIENT | PERCENTAGE BY WEIGHT |
| --- | --- |
| Water | 73.44% |
| Aloe Vera Gel | 2.50% |
| Walnut Oil | 2.00% |
| Tocopherol Acetate (Vitamin) | 2.00% |
| Glycerin | 2.00% |
| Stearic Acid | 2.00% |
| 1-Hexadecanol | 2.00% |
| Polysorbate-60 | 2.00% |
| Apricot Kernal Oil | 2.00% |
| Jojoba Oil | 2.00% |
| Glyceryl Stearate | 2.00% |
| PEG-100 Stearate | 1.00% |

| INGREDIENT | PERCENTAGE BY WEIGHT |
| --- | --- |
| Dimethicone | 1.00% |
| PVP | 1.00% |
| Hyaluronic Acid | 0.50% |
| Fibronectin | 0.50% |
| Sodium | 0.50% |
| Allantoin | 0.50% |
| Triethanolamine | 0.50% |
| Carbomer-940 | 0.20% |
| Chloride | 0.20% |
| Potassium | 0.05% |
| Urea 0.06% | |
| Calcium | 0.05% |
| Phosphate | 0.03% |
| Magnesium | 0.01% |

EXAMPLE II

A THERAPEUTIC SKIN GEL

A therapeutic skin gel is prepared by combining the following components utilizing conventional mixing techniques.

| INGREDIENT | PERCENTAGE BY WEIGHT |
| --- | --- |
| Water | 90.90% |
| Aloe vera extract | 2.00% |
| Glycerin | 2.00% |
| PVP | 1.00% |
| Triethanomine | 1.00% |
| Sodium | 0.70% |
| Hyaluronic Acid | 0.50% |
| Fibronectin | 0.50% |
| Allantoin | 0.50% |
| Carbomer-940 | 0.50% |
| Chloride | 0.20% |
| Potassium | 0.05% |
| Urea 0.06% | |
| Calcium | 0.05% |
| Phosphate | 0.03% |
| Magnesium | 0.01% |

EXAMPLE III—A THERAPEUTIC BODY CLEANSING LATHER

A therapeutic body cleansing lather is prepared by combining the following components utilizing conventional mixing techniques.

| INGREDIENT | PERCENTAGE BY WEIGHT |
| --- | --- |
| Water | 64.60% |
| Lecithin | 10.00% |
| Sodium Laureth Sulfate | 10.00% |
| Lauramide DEA | 5.00% |
| Cocamidopropyl Betaine | 3.00% |
| Glycerin | 2.00% |
| Aloe Vera gel | 2.00% |
| PVP 1.00% | |
| Allantoin | 0.50% |
| Sodium | 0.50% |
| Hyaluronic Acid | 0.50% |
| Fibronectin | 0.50% |
| Chloride | 0.20% |
| Potassium | 0.05% |
| Urea 0.06% | |
| Calcium | 0.05% |
| Phosphate | 0.03% |
| Magnesium | 0.01% |

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. The following claims are, therefore, to be read to include not only the combination of elements which are literally set forth, but all equivalent elements for performing substantially the same function in substantially the same way to obtain substantially the same result. The claims are thus to be understood to include what is specifically illustrated and described above, what is conceptionally equivalent, and also what essentially incorporates the germ of the invention.

I claim:

1. A substantially collagen-free composition for the treatment of chronic burns, open sores, incisions and wounds in human skin, said composition comprising:

medical grade hyaluronic acid;

tissue culture grade plasma fibronectin;

a topical solution comprising a mixture of four or more constituents selected from the group consisting of calcium, phosphate, uric acid, urea, sodium, potassium, chloride and magnesium, wherein said medical grade hyaluronic acid and said tissue culture grade plasma fibronectin are carried by said topical solution to the site of said burns, open sores, incisions and wounds to create a moist environment for optimum healing.

2. The composition of claim 1 wherein said topical solution comprises a pharmaceutically acceptable carrier.

3. The composition of claim 1 wherein said topical solution comprises a cosmetically acceptable carrier.

4. The composition of claim 1 wherein said medical grade hyaluronic acid comprises by weight 0.01% to 2.00% of said composition, wherein said tissue culture grade plasma-fibronectin comprises by weight 0.05% to 2.00% of said composition, and wherein said topical solution comprises by weight of said mixture:

0.01% to 1.50% calcium;

0.01% to 0.10% phosphate;

0.01% to 2.00% uric acid;

0.01% to 2.00% urea;

0.02% to 1.50% sodium;

0.01% to 0.10% potassium;

0.01% to 0.70% chloride; and 0.001% to 0.01% magnesium.

5. The composition of claim 1 wherein said medical grade hyaluronic acid comprises by weight 0.10% to 1.50% of said mixture, wherein said tissue culture grade plasma-fibronectin comprises by weight 0.020% to 1.50% of said mixture, and wherein said topical solution comprises by weight of said mixture:

0.50% to 1.00% calcium;

0.02% to 0.07% phosphate;

0.05% to 0.50% uric acid;

0.05% to 1.50% urea;

0.07% to 1.00% sodium;

0.02% to 0.06% potassium;

0.02% to 0.08% chloride; and 0.001% to 0.006% magnesium.

6. The composition of claim 1 wherein said medical grade hyaluronic acid comprises by weight 0.01% to 2.00% of said mixture, and wherein said tissue culture grade plasma-fibronectin comprises by weight 0.05% to 2.00% of said mixture.

7. The composition of claim 1 wherein said medical grade hyaluronic acid comprises by weight 0.20% to 1.50% of said mixture, and wherein said tissue culture grade plasma-fibronectin comprises by weight 0.020% to 1.50% of said mixture.

8. The composition of claim 1 wherein said topical solution comprises by weight of said mixture:

0.01% to 1.50% calcium;

0.01% to 0.10% phosphate;

0.01% to 2.00% uric acid;

0.01% to 2.00% urea;

0.02% to 1.50% sodium;

0.01% to 0.10% potassium;

0.01% to 0.70% chloride; and 0.001% to 0.01% magnesium.

9. The composition of claim 1 wherein said topical solution comprises by weight of said composition:

0.50% to 1.00% calcium;

0.02% to 0.07% phosphate;

0.05% to 0.50% uric acid;

0.05% to 1.50% urea;

0.07% to 1.00% sodium;

0.02% to 0.06% potassium;

0.02% to 0.08% chloride; and 0.001% to 0.006% magnesium.

10. The mixture of claim 1 further comprising pharmaceutical or cosmetic compositions.

11. The mixture of claim 1 further comprising cleaning compositions.

12. A substantially collagen-free composition for the treatment of chronic burns, open sores, incisions and wounds in human skin, said composition consisting essentially of:

medical grade hyaluronic acid; and tissue culture grade plasma fibronectin;

a topical solution, wherein said topical solution comprises a mixture of constituents comprising calcium, phosphate, uric acid, urea, sodium, potassium, chloride and magnesium, and wherein said medical grade hyaluronic acid and said tissue culture grade plasma fibronectin are carried by said topical solution to the site of said burns, open sores, incisions and wounds to create a moist environment for optimum healing.

13. The composition of claim 12 wherein said medical grade hyaluronic acid consists essentially by weight 0.01% to 2.00% of said composition, and wherein said tissue culture grade plasma-fibronectin consists essentially by weight 0.05% to 2.00% of said composition.

14. The composition of claim 12 wherein said medical grade hyaluronic acid consists essentially by weight 0.20% to 1.50% of said composition, and wherein said tissue culture grade plasma-fibronectin consists essentially by weight 0.020% to 1.50% of said composition.

15. An improvement in a method of healing comprising the step of:

delivering the substantially collagen-free composition of any of claims to a chronic burn, open sore, incision or wound in human skin so that a moist environment is created whereby optimum healing with minimal scarring is realized, where said step of delivering simulates the environment of amniotic fluid within said moist environment by providing said composition to maintain said optimum healing.

* * * * *